US006399685B1

(12) United States Patent
Klobucar et al.

(10) Patent No.: US 6,399,685 B1
(45) Date of Patent: Jun. 4, 2002

(54) PURIFICATION OF ARYLENE POLYPHOSPHATE ESTERS

(75) Inventors: W. Dirk Klobucar, Baton Rouge; William B. Harrod, Minden, both of LA (US); Billie B. Dadgar, Magnolia; Joseph D. McLean, Emerson, both of AR (US); Gary D. Heidebrecht, Orangeburg, SC (US); Hao V. Phan, Columbia, SC (US); Thomas R. Nicholas, Orangeburg, SC (US); Jeffrey L. Broeker, Orangeburg, SC (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/734,053

(22) Filed: Dec. 11, 2000

(51) Int. Cl.$^7$ .............................. C08K 5/52; C07F 9/12
(52) U.S. Cl. ...................... 524/145; 524/127; 558/162; 558/92
(58) Field of Search .................. 524/145, 127; 558/162, 92

(56) References Cited

U.S. PATENT DOCUMENTS

| | | | |
|---|---|---|---|
| 2,520,090 A | 8/1950 | Barrett | 260/461 |
| 3,174,931 A | 3/1965 | Matson et al. | 252/37.2 |
| 3,254,973 A | 6/1966 | Giammaria et al. | 4/69 |
| 3,317,636 A | 5/1967 | Lovell et al. | 260/929 |
| 3,360,591 A | 12/1967 | Giammaria et al. | 260/930 |
| 3,642,959 A | 2/1972 | Nichols | 260/929 |
| 4,107,232 A | 8/1978 | Haaf et al. | 360/876 R |
| 4,133,846 A | 1/1979 | Albright | 260/928 |
| 4,134,876 A | 1/1979 | Horner et al. | 260/45.7 P |
| 4,223,100 A | 9/1980 | Reinert | 525/146 |
| 4,343,732 A | 8/1982 | Zama et al. | 524/114 |
| 4,463,130 A | 7/1984 | Serini et al. | 525/67 |
| 4,692,488 A | 9/1987 | Kress et al. | 524/139 |
| 4,837,276 A | 6/1989 | Fuhr et al. | 524/125 |
| 4,966,814 A | 10/1990 | Ohzeki | 428/457 |
| 5,061,745 A | 10/1991 | Whittmann et al. | 524/139 |
| 5,204,394 A | 4/1993 | Gosens et al. | 524/125 |
| 5,278,212 A | 1/1994 | Nishihara et al. | 524/141 |
| 5,281,741 A | 1/1994 | Gunkel et al. | 558/92 |
| 5,391,690 A | 2/1995 | Kanno et al. | 528/198 |
| 5,420,327 A | 5/1995 | Bright et al. | 558/99 |
| 5,455,292 A | 10/1995 | Kakegawa et al. | 525/141 |
| 5,457,221 A | 10/1995 | Brady et al. | 558/99 |
| 5,663,280 A | 9/1997 | Ogoe et al. | 528/196 |
| 5,672,645 A | 9/1997 | Eckel et al. | 524/127 |
| 5,750,756 A | 5/1998 | Bright et al. | 558/162 |
| 5,756,798 A | 5/1998 | Stults | 558/99 |
| RE36,188 E | 4/1999 | Gosens et al. | 524/125 |
| 5,952,408 A | 9/1999 | Lee et al. | 524/127 |
| 6,011,184 A * | 1/2000 | Aarssen et al. | 568/722 |
| 6,093,760 A * | 7/2000 | Nishihara et al. | 524/145 |
| 6,319,432 B1 * | 11/2001 | Harrod et al. | 252/609 |

FOREIGN PATENT DOCUMENTS

| | | |
|---|---|---|
| EP | 0074112 B2 | 3/1983 |
| EP | 0074112 A1 | 3/1983 |
| EP | 0103230 | 3/1984 |
| EP | 0491986 | 7/1992 |
| EP | 0767204 | 4/1997 |
| EP | 0936243 | 8/1999 |
| GB | 734767 | 8/1955 |
| GB | 1027059 | 4/1966 |
| GB | 2043083 | 10/1980 |
| JP | 5051154 | 5/1975 |
| JP | 5924736 | 2/1984 |
| JP | 5945351 | 3/1984 |
| JP | 59202240 | 11/1984 |
| JP | 63117057 | 5/1988 |
| JP | 63227632 | 9/1988 |
| JP | 5186681 | 7/1993 |
| JP | 1025298 | 1/1998 |
| WO | 9613508 | 5/1996 |
| WO | 9617853 | 6/1996 |
| WO | 9747631 | 12/1997 |
| WO | 9835970 | 8/1998 |
| WO | 9911713 | 3/1999 |
| WO | 9955771 | 11/1999 |

OTHER PUBLICATIONS

Burckhardt Helferich and Karl Gunther Schmidt, "Esters and Polyesters of Phosphoric Acids and Cycloalkylphosphonic Acids with Phenols," Chemical Institute, Bonn University, Chem. Ber. 92, pp 2051–2056 (w/translation), (1959).
Caplus Abstract of Romania Patent 71829; 1982.
Caplus Abstract of Japan Patent 51103195; 1976.
Caplus Abstract of Japan Patent 57174331; 1982.
Caplus Abstract of Japan Patent 59202240; 1984.
Caplus Abstract of Japan Patent 63227632; 1988.
Caplus Abstract of Romania Patent 64218, 1978.
Caplus Abstract of Romania Patent 63976; 1978.

* cited by examiner

Primary Examiner—Deborah C. Lambkin
(74) Attorney, Agent, or Firm—E. E. Spielman, Jr.

(57) ABSTRACT

Emulsion formation is minimized or prevented and hydrolytic product degradation is suppressed during purification of impure bisphenol-A bis(diphenylphosphate). This is accomplished by forming a hydrocarbon solution of bisphenol-A bis(diphenylphosphate) plus impurities in a solvent comprising at least one aromatic hydrocarbon and at least one paraffinic hydrocarbon. Optionally, but preferably, this solution is washed with water or an aqueous buffer solution. Next, the hydrocarbon solution is washed one or more times with an aqueous alkaline washing solution that has a specific gravity that differs from the specific gravity of the hydrocarbon solution by at least about 0.05 gram per cubic centimeter. After each washing the mixture settles into a purified organic phase and a separate aqueous phase, and these phases are separated from each other. After completing the one or more alkaline washings and separations, the resultant purified organic phase is washed one or more times with water to remove alkaline components from the hydrocarbon solution, and after each such washing the washed mixture is settled into a less alkaline purified organic phase and a separate aqueous phase. These phases are separated, and preferably the purified product is recovered from the organic phase.

51 Claims, No Drawings

PURIFICATION OF ARYLENE POLYPHOSPHATE ESTERS

BACKGROUND

Arylene polyphosphate esters such as bisphenol-A bis (diphenylphosphate) are useful as flame retardants for various polymeric materials. Reported methods for their preparation typically involve reacting a diphenolic compound such as bisphenol-A with a diarylphosphoryl halide such as diphenylphosphoryl chloride. In such synthesis operations the product as produced is associated with various impurities such as unreacted starting material, partially phosphorylated product, acidic impurities, color bodies, and/or catalyst residues. Washing procedures that have been used to remove such impurities are of ten plagued by the formation of emulsions. See for example, U.S. Pat. Nos. 3,254,973; 5,420,327; and 5,756,798; and WO 98/35970, published Aug. 20, 1998.

The purification of bisphenol-A bis(diphenylphosphate) is complicated by the fact that not only is there the possibility of emulsion formation but in addition, during washing procedures product losses due to hydrolytic degradation can occur. Emulsions, even if formed sporadically, can consume considerable time and effort in effectively dealing with them. Hydrolytic degradation, if experienced, cannot be undone; product loss is inevitable. Moreover, crude bisphenol-A bis(diphenylphosphate) as formed is a viscous liquid and thus the removal of impurities from impure or crude bisphenol-A bis(diphenylphosphate) reaction product is not an easy proposition. Thus the provision of an effective way of reducing or preventing the formation of emulsions and of suppressing hydrolysis during the purification of impure bisphenol-A bis(diphenylphosphate) would be of considerable advantage.

BRIEF SUMMARY OF THE INVENTION

This invention is deemed to provide an effective and efficient way of reducing or preventing the formation of emulsions and of suppressing hydrolysis during the purification of impure bisphenol-A bis(diphenylphosphate). The process technology of this invention is readily adaptable for use on an industrial scale, and is deemed independent of the particular process technology used in forming the impure product. Moreover, the process technology does not require large capital investments or involve excessive operating costs.

In one of its embodiments this invention is a process of minimizing or preventing emulsion formation and suppressing hydrolytic product degradation during the purification of an impure bisphenol-A bis(diphenylphosphate) product, which process comprises:

a) mixing such impure product with a liquid hydrocarbon solvent comprising at least one aromatic hydrocarbon and at least one paraffinic hydrocarbon in proportions of such impure product to such liquid hydrocarbon solvent in the range of about 25:75 to about 75:25 to form a hydrocarbon solution;

b) washing hydrocarbon solution from a) one or more times with an aqueous alkaline washing solution that has a specific gravity that differs from the specific gravity of the hydrocarbon solution by at least about 0.05 gram per cubic centimeter, after each such washing having the washed mixture settle into a purified organic phase and a separate aqueous phase, and separating these phases from each other, each such washing and separating being performed with the phases at a temperature in the range of about 25 to about 100° C.; and c) after completing the one or more washings and separations in b), washing the resultant purified organic phase one or more times with water to remove alkaline components from the hydrocarbon solution, after each such washing having the washed mixture settle into a less alkaline purified organic phase and a separate aqueous phase, and separating these phases from each other, each such washing and separating being performed with the phases at a temperature in the range of about 25 to about 100° C.

The paraffinic hydrocarbon(s) used in forming the liquid hydrocarbon solvents employed in the practice of this invention can be (i) one or more cyclic paraffinic hydrocarbons (i.e., at least one cycloparaffinic hydrocarbon), (ii) one or more acyclic paraffinic hydrocarbons, or (iii) a mixture of (i) and (ii).

In preferred embodiments this invention is a process of minimizing or preventing emulsion formation and suppressing hydrolytic product degradation during the purification of an impure bisphenol-A bis(diphenylphosphate) product, which process comprises:

1) mixing (i) an aqueous buffer solution, or a dilute acid wash, or a water wash, the pH of any of which is less than about 5.5, with (ii) the impure product in the presence of a liquid hydrocarbon solvent comprising at least one aromatic hydrocarbon and at least one paraffinic hydrocarbon in proportions of impure product to such liquid hydrocarbon solvent in the range of about 25:75 to about 75:25, and then having the mixture settle into an organic phase and a separate aqueous phase, and separating these phases from each other;

2) washing organic phase from 1) one or more times with an aqueous alkaline washing solution that has a specific gravity that differs from the specific gravity of the organic phase by at least about 0.05 gram per cubic centimeter, after each such washing having the washed mixture settle into a purified organic phase and a separate aqueous phase, and separating these phases from each other, each such washing and separating in 2) being performed with the phases at a temperature in the range of about 25 to about 100° C.; and 3) after completing the one or more washings and separations in 2), washing the resultant purified organic phase one or more times with water to remove alkaline components from the hydrocarbon solution, after each such washing having the washed mixture settle into a less alkaline purified organic phase and a separate aqueous phase, and separating these phases from each other, each such washing and separating in 3) being performed with the phases at a temperature in the range of about 25 to about 100° C.

If in the above embodiments there are solids present in the solution formed either in a) or in 1), these can be separated as by filtration, decantation, or centrifugation. Although the number of times each of b) and c) above, or each of 2) and 3) above, is conducted depends on various factors such as the scale of operation and the relative quantities of aqueous washing liquids to organic phase, in a plant scale operation b) above or 2) above will typically be conducted twice, and c) above or 3) above will typically be conducted from two to three times as needed to suitably remove the alkaline residues from the purified product. When conducting b) above or 2) above at least twice, it is preferred that the concentration of the base such as sodium hydroxide in the first alkaline washing solution be higher than in the ensuing alkaline washing solution(s).

In the practice of the above embodiments, the times required in b) and c) above, or in 2) and 3) above, for the phases to separate and settle is typically quite short. For example, on a one-liter scale, each such separation and settling into separate liquid phases can occur in as little as about 1 to 2 minutes after agitation has been terminated.

If it is desired to isolate the purified bisphenol-A bis(diphenylphosphate) product, the final organic phase from c) above or 3) above is treated to remove the organic solvent. This can be readily accomplished either in vacuo and/or by removing the solvent(s) by azeotropic or steam distillation.

In particularly preferred embodiments, the organic solvent used is a mixture comprising in the range of about 10 to about 70 wt % of toluene, and in the range of about 10 to about 70 wt % of at least one liquid cycloparaffinic hydrocarbon, most preferably cyclohexane or methylcyclohexane, or both, with the total of these components being at least 90 wt %, with the balance, if any, to 100% being at least one other aromatic hydrocarbon. An especially preferred organic solvent is a liquid mixture consisting essentially of (i) toluene and (ii) cyclohexane or methylcyclohexane, or both, in a weight ratio of (i):(ii) in the range of about 30:70 to about 70:30. It is also particularly preferred to employ as the aqueous alkaline washing solution, an aqueous alkali metal hydroxide solution, and especially an aqueous sodium hydroxide solution.

The above and other features and embodiments of this invention will be still further apparent from the ensuing description and appended claims.

FURTHER DETAILED DESCRIPTION

Bisphenol-A bis(diphenylphosphate) which can be effectively purified by use of this invention can be represented by the formula

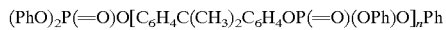

where Ph is phenyl, $C_6H_4$ is a p-phenylene group, and n is a number in the range of 0 to about 5 with the provisos that (A) if the depicted phosphate is a single compound, then n is 1, 2, 3, 4, or 5, and (B) if the depicted phosphate is a mixture of such depicted phosphate esters in which the numerical values for n are not the same for each molecule of the mixture, then n can (but need not) include zero, and is the average number for such mixture and is in the range of about 1 to below 5, preferably is between 1 and about 2, and most preferably is between 1 and about 1.5. That is, where the product to be purified is a mixture, some triphenylphosphate can be present along with compounds of the above formula where n is, for example, 1, 2 and 3. In addition, at least 90 wt % of the balance, if any, to 100 wt % is composed of other phosphorus-containing species.

A preferred product formed by use of the process of this invention consists essentially of at least about 78–87 wt % of compound of the above formula where n is 1; at least about 11–12 wt % of compound of the above formula where n is 2; at least about 1 to about 1.5 wt % of compound of the above formula where n is 3; about 0–1.5 wt % of compound of the above formula where n is zero (i.e., triphenylphosphate); and at least 90 wt % of the balance, if any, to 100 wt % being other phosphorus-containing species. These are excellent flame retardant compositions.

As an example of the efficiency of the process technology of this invention, it has been found possible to convert a crude bisphenol-A bis(diphenylphosphate) reaction product comprised of about 69.5 wt % of compound of the above formula where n is 1, into a product of this invention consisting essentially of 84.66 wt % of compound of the above formula where n is 1; 11.99 wt % of compound of the above formula where n is 2; 1.46 wt % of compound of the above formula where n is 3; less than 100 ppm of isopropenylphenyl diphenylphosphate; 0.11 wt % of bisphenol-A mono(diphenylphosphate); and 0.27 wt % of diphenylphosphate, with at least 90 wt % of the balance to 100 wt % being other phosphorus-containing species.

This invention is applicable to the purification of bisphenol-A bis(diphenylphosphate) produced by any of a variety of synthesis procedures, such as procedures of the types described, for example, in U.S. Pat. Nos. 2,520,090; 3,254,973; 4,343,732; 5,281,741; 5,420,327; or 5,756,798; or in WO 96/13508; or WO 96/17853; or in Japan Kokai Nos. 51/103195 A2; 51/174331 A2; 59/202240 A2; 63/227632 A2; or 05/186681 A2. The important thing is that the impure or crude product has associated with it one, or typically more than one, impurity such as one or more acid impurities, color bodies, unreacted starting materials, partially phosphorylated intermediates, residual catalyst, catalyst residues, halide impurities, or the like. In this connection, the words "impure" and "crude" are used interchangeably in this document to denote that the product being purified contains one or more such impurities.

It is preferred that the impure or crude product mixture not be subjected to an alkaline wash prior to conducting a) or 1) above. Such a wash tends to engender reaction of the base with any phenolic species present as impurities to thereby form products having surfactant properties. This in turn can cause a hydrolysis and/or an emulsion to form. Instead, it is preferable to subject the impure or crude product mixture to one or more washings with water, or with an aqueous buffer solution having a pH of less than about 5. This is accomplished by thoroughly mixing (i) an aqueous buffer solution with a pH of less than about 5, or water with (ii) the impure or crude product mixture in the presence of the liquid hydrocarbon solvent comprising at least one aromatic hydrocarbon and at least one paraffinic hydrocarbon in proportions of impure product mixture to such liquid hydrocarbon solvent in the range of about 25:75 to about 75:25, and then having the mixture settle into an organic phase and a separate aqueous phase, and separating these phases from each other. Thereafter 2) and 3) above are, of course, carried out. Some of the advantages of using such water wash or aqueous buffer wash in the process include:

1) Fast phase separation of the organic layer containing the washed crude product and the aqueous layer from such washing which contains catalyst residues and phosphoric acid-type impurities.

2) Virtual elimination of emulsion formation that would require reworking which is both time-consuming and costly.

3) Cycle time in the overall process is greatly improved and thus manufacturing cost is reduced.

4) At most, only low levels of metal impurities are present in the final purified product.

5) Further reductions in phenolic impurities in the final purified product can be achieved.

6) Final product with a low acid number can be produced. While various aqueous buffer solutions with pH below about 5.5 can be used as the washing solution, use of aqueous phosphate-containing buffer solution with pH below about 5.5 are preferred. Use of an aqueous buffer solution is desirable when performing the washing in vessels susceptible to corrosion by contact with acidic liquid media. Among suitable dilute acid washes with pH below about 5.5 that can be used are mineral acids, water-soluble organic acids, and acidic salts. A few examples include hydrochloric acid, sulfuric acid, phosphoric acid, methanesulfonic acid, and sodium dihydrogen phosphate. Dilute sulfuric acid is one of the preferred dilute acid washes. A typical water wash with a pH below about 5.5 is water containing dissolved carbon dioxide, ie., carbonated water.

The amount of aqueous buffer solution, dilute acid wash, or water wash used in the initial aqueous buffer wash, dilute acid wash or water wash is not critical as long as enough of such wash is used to carry out an effective washing operation. Minimally, at least about 5–10 pounds of the buffer wash solution, dilute acid wash, or water wash can be used per each 100 pounds of the crude or impure product. Desirably, the ratio of the buffer wash, dilute acid wash, or water wash to the crude or impure product will be higher than this. For example, ratios in the range of up to at least about 20–50 pounds of the wash per each 100 pounds of crude or impure product can be used.

In conducting this optional, but preferred, initial aqueous buffer wash, or dilute acid wash, or water wash it is important to ensure that any substantial amount of the wash does not come in contact with the crude or impure product mixture in the absence of hydrocarbon solvent. Thus one suitable feeding procedure is to feed the wash being used into the washing vessel after the hydrocarbon solvent and the crude or impure product mixture have been charged into the vessel and mixed together, e.g., by charging these components in the following order: 1) hydrocarbon solvent, 2) crude or impure product mixture, and 3) aqueous buffer wash, or dilute acid wash, or water wash. Another suitable feeding procedure for this optional, but preferred, initial washing operation is to feed the crude or impure product mixture into the vessel which already contains the wash being used and the hydrocarbon solvent. As noted above the hydrocarbon solvent used comprises at least one aromatic hydrocarbon and at least one paraffinic hydrocarbon. Other feasible ways of feeding hydrocarbon solvent, crude or impure product mixture, and aqueous buffer wash, or dilute acid wash, or water wash may be used provided that the performance of the process in minimizing or preventing emulsion formation and suppressing hydrolytic product degradation during the purification is not materially interfered with.

Mixed liquid hydrocarbon solvents used in the practice of this invention comprise at least one aromatic hydrocarbon and at least one paraffinic hydrocarbon. It is not essential that each component making up the solvent mixture be a liquid at 20° C. provided the mixture itself is in the liquid state at 20° C. Preferably however each of the components of the solvent mixture is a liquid at 20° C. Typically the mixture will comprise at least 50 wt %, and preferably at least 65 wt % of the combination of aromatic and paraffinic hydrocarbon components. The balance, if any, can be one or more other suitable non-polar or essentially non-polar solvent components, such as olefinic or cycloolefinic hydrocarbons (e.g., one or more isomeric forms of hexene, heptene, octene, nonene, decene, undecene, dodecene, cyclopentene, cyclohexene, methylcyclohexene or the like, or mixtures of any two or more of olefinic and/or cycloolefinic hydrocarbons such as the foregoing. The relative proportions of aromatic hydrocarbon to paraffinic hydrocarbon will depend on such factors as the target specific gravity of the solution to be formed in a) or 1) above, the specific gravity of the aqueous alkaline solution being used in b) or 2) above, and, of course, the specific gravities of the aromatic and paraffinic components themselves. Thus in any given situation where the appropriate relative proportions of the aromatic and paraffinic components has not been previously ascertained, a few pilot experiments should be conducted to develop the appropriate relative proportions.

Examples of suitable aromatic hydrocarbons for use in forming the mixed aromatic-paraffinic hydrocarbon solvent composition include benzene, toluene, xylene, ethylbenzene, propylbenzene, cumene, isobutylbenzene, isohexylbenzene, amylbenzene, tert-amylbenzene, pentaethylbenzene, 1-methylnaphthalene, 1,2,3,4-tetrahydronaphthalene and analogous aromatic hydrocarbons, which typically contain up to about 18 carbon atoms in the molecule, but which may contain any number of carbon atoms as long as the resultant mixed aromatic-paraffinic solvent composition is a free-flowing liquid at the temperature at which the mixed solvent composition is employed.

Cycloparaffinic hydrocarbons suitable for use in forming the mixed aromatic-paraffinic hydrocarbon solvent composition include cyclopentane, methylcyclopentane, cyclohexane, methylcyclohexane, 1,3-dimethylcyclohexane, 1,4-dimethylcyclohexane, isopropylcyclohexane, p-menthane, 1,3,5-trimethylcyclohexane, and analogous cycloparaffinic hydrocarbons, which typically contain up to about 14–16 carbon atoms in the molecule. However, the cycloparaffinic hydrocarbon(s) may contain any number of carbon atoms as long as the resultant mixed aromatic-paraffinic solvent composition is a free-flowing liquid at the temperature at which the mixed hydrocarbon solvent composition is employed.

Acyclic paraffinic hydrocarbons suitable for use in forming the mixed aromatic-paraffinic hydrocarbon solvent composition include, for example, such compounds as any of the isomeric forms of pentane, hexane, heptane, octane, nonane, decane, undecane, dodecane, and their higher homologs. Typically these hydrocarbons contain up to about 14–16 carbon atoms in the molecule, but they may contain any number of carbon atoms as long as the resultant mixed aromatic-paraffinic hydrocarbon solvent composition is a free-flowing liquid at the temperature at which the mixed solvent composition is employed.

Preferred mixed aromatic-paraffinic hydrocarbon solvent mixtures are free-flowing liquid mixtures composed of (A) one or more aromatic hydrocarbons and one or more cycloparaffinic hydrocarbons, or (B) one or more aromatic hydrocarbons, one or more cycloparaffinic hydrocarbons, and one or more acyclic paraffinic hydrocarbons, in which at least 50 wt % of the paraffinic portion of the aromatic-paraffinic hydrocarbon mixture is one or more cycloparaffinic hydrocarbons.

Preferably the aromatic-paraffinic hydrocarbon solvent mixture should be a composition that will distill, either azeotropically or with the aid of steam and/or vacuum, at a temperature below about 160° C., and more preferably below about 130° C.

A more preferred solvent mixture is a liquid mixture comprising in the range of about 10 to about 70 wt % percent of at least one aromatic hydrocarbon and in the range of about 10 to about 70 wt % percent of at least one cycloparaffinic hydrocarbon, with the total of these components being at least 90 wt % and preferably 100 wt % of the hydrocarbon mixture. A still more preferred liquid solvent mixture is comprises in the range of about 10 to about 70 wt % percent of toluene and in the range of about 10 to about 70 wt % percent of at least one cycloparaffinic hydrocarbon, with the total of these components being at least 90 wt %, with the balance, if any, to 100% being at least one other aromatic hydrocarbon. Particularly preferred is a liquid mixture consisting essentially of (i) toluene and (ii) cyclohexane or methylcyclohexane, or both, in a weight ratio of (i):(ii) in the range of about 30:70 to about 70:30.

It is within the purview of this invention to include non-hydrocarbonaceous components in the mixed aromatic-paraffinic hydrocarbon solvent mixture as long as such components do not in any way detract from the performance of the mixed solvent composition. The inclusion of such components, although permissible, is not recommended.

To minimize the risk of emulsion formation, the entire quantity of the crude product mixture should be dissolved in the hydrocarbon solvent mixture before initiating the washing step(s) using an aqueous alkaline washing solution. Better still, the entire quantity of the crude product should be washed with water or an aqueous buffer solution in the presence of the hydrocarbon solvent mixture in the manner described above before initiating the step(s) of washing the hydrocarbon solution of the product mixture with an aqueous alkaline washing solution. If any of the crude product remains undissolved in the hydrocarbon solvent mixture, there is a distinct possibility that excessive amounts of emulsions may be formed during such alkaline washing step, and thus such undissolved material should be removed. Preferably, the solution of the crude product in the hydrocarbon solvent mixture should have a solvent loading (i.e., the solution should contain) in the range of about 25 to about 75 wt % of completely dissolved crude product as a homogeneous solution. Any solids in the solution are preferably removed by filtration or the like.

The aqueous alkaline washing solution used in b) or 2) above contains inorganic base in solution, typically an inorganic base of an alkali metal or an alkaline earth metal, or both. Examples of suitable bases which can be used in forming the aqueous washing solution include lithium oxide, sodium oxide, potassium oxide, lithium hydroxide, sodium hydroxide, potassium hydroxide, potassium carbonate, barium oxide, barium hydroxide, and similar compounds. Of these, the alkali metal oxides are preferred starting materials as they form hydroxides in water, and the alkali metal hydroxides, especially potassium hydroxide and most especially sodium hydroxide, are particularly preferred starting materials. Other suitable inorganic bases such as ammonia or ammonium hydroxide maybe used. Usually the washing solution used in b) or 2) above has dissolved therein approximately 0.1–15 wt % of alkali metal oxide, hydroxide, or carbonate, or the corresponding molar equivalent of other suitable base. Aqueous solutions in the range of about 0.1 to about 15 wt % of sodium hydroxide are highly suitable because of their excellent effectiveness and low cost.

The washing operation(s) in b) or 2) above are typically performed at one or more temperatures in the range of about 25 and about 100° C., and preferably in the range of about 45 and about 75° C. In addition, it is preferred to coordinate (i) the solvent loading of the solution of crude produce in the hydrocarbon solvent mixture, with (ii) the wash operating temperature(s) being used. Proper coordination of these variables can significantly reduce the possibility of problems arising with respect to solubility and/or emulsion formation during the washing operations of b) above or 2) above. For example, when using a 42% loading of crude bisphenol-A bis(diphenylphosphate) in a mixed hydrocarbon solvent of this invention, the washing temperature should be kept above about 40° C. in order to prevent problems with solubility and the emulsions which result. Solvent loadings above 42 wt % enable the washing operations to be conducted at progressively lower wash operating temperatures without incurring solubility or emulsion problems. In any given situation where optimal coordinated solvent loading and washing temperature conditions have not been previously ascertained, it is a simple matter to perform a few preliminary tests to ascertain optimal coordinated conditions for use in such situation.

Mixing in c) or 3) above should be of sufficient intensity and duration to ensure thorough contact between and among the components. The mixture should thus be agitated by suitable stirring means or shaking means such as, for example, a mechanical stirrer or a mechanical shaker. Mixing is typically conducted with the mixture at a temperature in the range of about 25 to about 100° C., and preferably in the range of about 45 to about 75° C.

After the mixing in c) or 3) above, the mixture is allowed to settle while in a quiescent state whereby the organic and aqueous phases separate into two distinct layers. If the operation is properly conducted there will be little if any rag between the phases. Thereafter the phases can be separated from each other by draining or decanting one phase layer from the other. Usually, and preferably, the organic layer will be superposed on the underlying aqueous layer thus enabling the aqueous layer with the impurities therein to be drained from the washing vessel. This enables the purified bisphenol-A bis(diphenylphosphate) to be recovered from the organic solution by vaporizing or distilling off the solvent without transferring the solution from the mixing vessel. The vaporized solvent is preferably condensed and collected for reuse in the process.

Preferably, the purified bisphenol-A bis (diphenylphosphate) and the hydrocarbon solvents are separated by use of in situ or live steam stripping for efficient removal of the hydrocarbon solvents used as the organic medium for the alkaline washes. For this purpose an external supply of steam can be introduced into the solution or water can be added to the solution and the resultant mixture heated to generate the steam in situ. A vacuum is typically applied to expedite this stripping operation. The use or in situ generation of steam allows the solvent strip to be performed in less processing time, e.g., two hours versus 12 hours for standard flash at the same operating temperature. Also, use or in situ generation of steam enables the separation to be performed at lower temperatures (e.g., about 35 to about 130° C., and/or higher pressures (e.g., about 0 to about 100 mm Hg absolute). Use of such lower temperatures minimizes product degradation caused by use of higher temperatures and eliminates the need for more costly vacuum equipment (e.g., vacuum pumps and/or wiped film evaporators).

It is also preferred to conduct the process operations of this invention in an inert environment, such as under a nitrogen blanket or blanket of other inert gas such as argon. By operating in this manner, haze formation or development of turbidity can be minimized, if not eliminated.

When the process technology of this invention is properly conducted, the competing reaction of hydrolysis of bisphenol-A bis(diphenylphosphate) is suppressed, even when separating the solvent from the purified bisphenol-A bis(diphenylphosphate) by steam distillation. Hence yield losses due to hydrolysis of the bisphenol-A bis (diphenylphosphate) during the entire purification operation are minimal. Without desiring to be bound by theory, it is believed that the suppression of hydrolysis during the washing step and, in the most severe case, during steam distillation is due to the low polarity of solvent mixture.

The following illustrative Examples are not intended to limit, and should not be construed as limiting, the generic scope of this invention. Example I–V are for comparative purposes. Examples VI–XV illustrate the invention. In these Examples all percentages are by weight, and the following acronyms are used:

BPADP is bisphenol-A bis(diphenylphosphate);
BPA is bisphenol-A;
TPP is triphenylphosphate;
IPP is isopropenylphenyl diphenylphosphate; and
DPP is diphenylphosphate.

References to n are to the number of repeating moieties in the oligomers, such number being designated as n in the formula presented hereinabove.

COMPARATIVE EXAMPLE I
No Solvent Used

An attempted purification without use of a solvent was performed by adding 59.8 g of crude BPADP and 202.53 g of 11.1% aqueous NaOH solution into a 500 mL Erlenmeyer flask and stirred at 64° C. for 30 minutes. An opaque emulsified organic portion was observed. The total organic portion was increased to 116.16 g by addition of 56.4 g crude BPADP. The densities were measured: 1.18 g/mL for the organic phase and 1.11 g/mL for the aqueous portion. An attempt was made to wash this with 200 mL water at 65° C. whereupon a single emulsified liquid phase was obtained. The emulsion broke in three days at 25° C. and the mixture was discarded.

COMPARATIVE EXAMPLE II
Use of Alkanol Wash

Isopropyl alcohol, 150 mL, and a total of 40.5 g of crude BPADP (added in portions) were washed with 50 mL 25% NaOH initially at 25–35° C. in a jacketed three-necked 1 L round-bottom flask equipped with stirrer, a thermometer and a gas inlet tube (tee) to maintain atmospheric pressure. Five minutes after the last portion of BPADP was added, a very slow separation into two liquid phases was observed. Then 104.07 g organic was obtained which had a density of 1.09 g/mL. A viscous aqueous phase was obtained with its density being (0.99 g/mL). The unreacted base concentration in the sample was 11.45%, titrated as NaOH. Owing to the difficulty of phase separation the mixture was discarded.

COMPARATIVE EXAMPLE III
Effect of loading and Temperature

A 160.2 g portion of crude BPADP was dissolved in 150 mL of a 50% solution of toluene and 50% of methylcyclohexane (MCH). It was observed that the BPADP was not soluble at 25° C. in this mixture yet almost all dissolved upon heating to 70° C. The organic was washed with 75 mL of 25% NaOH which was fed slowly by addition funnel into a stirred 500 mL three-necked round-bottom flask. A mild exotherm was noted and upon completing the wash, a gray off-white sludge was obtained, as a single liquid phase, and discarded.

COMPARATIVE EXAMPLE IV
Effect of NaOH concentration Using Toluene Alone

Crude BPADP was added, as 339 g of a 45% solution in toluene, into a stirred jacketed three-necked 1 L flask and stirred at 80° C. After temperature equilibration, 130 mL of aqueous NaOH (5.5% wt) was added and the organic phase was washed with high agitation for 25 minutes at 74–77° C. after which the agitation was ceased and a milky emulsion was noted. Methylcyclohexane (100 mL) was added, the solution was remixed and then upon ceasing agitation, a clean phase separation was seen in about one minute. The organic phase was washed three times with 200 mL portions of water, then dried and analyzed by HPLC. This showed BPADP 88.3%, phenol 0.7% (incomplete removal), BPA 2.4%, TPP 1.2%.

COMPARATIVE EXAMPLE V
Order of Addition

A 1000-mL jacketed round-bottom flask with a bottom outlet and equipped with a mechanical agitator, a thermometer, and a condenser was charged with 384.87 g of 50/50 (wt/wt) toluene/methylcyclohexane (MCH) and 121.60 g of 10% NaOH. With the temperature of the mixture being maintained at 55° C., a BPADP synthesis reaction mass (274.24 g) at~70° C. was then charged into the mixture. The contents were agitated at 55° C. for 30 minutes and then settled for 30 minutes. The bottom aqueous layer (138.92 g) was separated from the organic layer through the bottom outlet. To remove the remaining phenol, another NaOH wash (1%, 119.80 g) was conducted in the same way as the 10% NaOH wash. The phase cut (146.15 g) of this wash was not clean, with a lot of rag and bubbles.

Examples VI–XV demonstrate the practice, characteristics, and advantageous features of the invention.

EXAMPLE VI

Crude BPADP (1362 g) was purified in a jacketed wash kettle (5 liter 4 necked flask with a bottom drain and a mechanical stirrer) by first dissolving in a mixture of 1000 g of toluene and 1004 g of methylcyclohexane. The solution was then washed at 60–72° C. with 300 g of 10 wt % aqueous potassium hydroxide (obtained 434 g of aqueous phase, pH~14), 300 g of 5 wt % aqueous potassium hydroxide (obtained 334 g of aqueous phase, pH~14), 301 g of tap water (obtained 304 g of aqueous phase, pH~11), 302 g of tap water (obtained 304 g of aqueous phase, pH~8), and then 302 g of tap water (obtained 307 g of aqueous phase, pH~7). A portion of this mixture (1621 g) was taken, filtered (Whatman 2v paper) and the volatiles were removed (2 torr/90° C.). The residual solvent was removed in a vacuum oven at 150° C./2 torr to give 607 g of slight cloudy colorless product as a viscous oil. The product by HPLC analysis contained 0.07% DPP, 0.49% half-ester, 0.002% IPP, 84.17% BPADP, 12.35% dimer, and 1.53% trimer. The table below displays the analytical results of the BPADP mixture before and after the washes and demonstrates the utility and efficiency of the purification with respect to acid number, metals, total chlorides, and phenol content.

|  | BPADP Crude (before wash) | BPADP (after wash) |
| --- | --- | --- |
| Phenol, wt % | 3.4 | 0.05 |
| Acid number, mg KOH/g | 26 | 0.12 |
| Mg, ppm | 617 | 0.029 |
| Na, ppm | 1.6 | 0.15 |
| Fe, pp, | 0.7 | 0.0006 |
| Total Cl, ppm | 70 | <0.001 |

EXAMPLE VII

Crude BPADP was purified by dissolving 286.4 g of BPADP into 483.5 g of mixed solvent (50% of methylcyclohexane and 50% of toluene), then washing with two 150 g portions 10% NaOH, with phase separation at 70° C. of the aqueous phase after each wash using a stirred 1-L jacketed three-necked round-bottom flask with bottom valve for liquids removal. The organic phase was then washed with three portions of water at 70° C., then separated from the aqueous layer. Solvent removal and drying of the organic were accomplished by distillation and nitrogen stripping. The organic recovery in the purification step was 91.3% wt. The residual solvent was removed in a vacuum oven (12 hours, 30 mm Hg; 140° C.). HPLC of the acidic crude BPADP starting material showed 69.92% BPADP, 9.07% oligomerics, 11.0% unknowns, 2.35% PhOH, no TPP was detected, and the IPP level was <0.01%. By contrast, HPLC of the purified organic portion showed 84.66% BPADP, 11.99% oligomer (n=2), 1.46% oligomer (n=3), <0.01% isopropenylphenyl diphenylphosphate (IPP), 0.11% diphenylphosphate of bisphenol-A, 0.27% DPP. The acidity of the purified organic was measured as being less than 0.05% wt. HCl, as determined by titration using 0.1N NaOH.

EXAMPLE VIII

Crude BPADP (201.3 g) was dissolved in 1:1 toluene:methylcyclohexane (495.3 g) and washed at 70° C. twice with 140 mL portions 10% NaOH, and then three times with 150 mL portions of water using the procedure described in Example VI. Analyses of the crude BPADP prior to washing showed 67.56% BPADP, 5.5% wt phenol, no IPP, 3.23% diphenylphosphate (DPP), 10.24% oligomer (n=2), 1.25% oligomer (n=3). After the described workup, HPLC analyses showed 80.5% BPADP, 11.93% oligomer n=2, 1.57% n=3, <0.01% IPP, 0.17% DPP, no toluene nor phenol, 1.6% triphenylphosphate (TPP). The aqueous portions were analyzed for phenol (HPLC) and phosphorus (by X-ray fluorescence) and those results are shown in Table 1 below.

TABLE 1

Analysis of Aqueous Portions from Purification of BPADP (Example VIII).

| Sample | Description | Wt % Phenol | Wt % Phosphorus |
| --- | --- | --- | --- |
| 1 | NaOH, 1st wash | 7.12 | 0.85 |
| 2 | NaOH, 2nd wash | 0.72 | 0.1 |
| 3 | Water, 1st wash | 0.03 | 0.05 |
| 4 | Water, 2nd wash | <0.01 | 0.02 |
| 5 | Water, 3rd wash | <0.01 | <0.01 |

EXAMPLE IX

In this two-part experiment, the effect of toluene:methylcyclohexane ratio was explored.

Part A: BPADP crude product 144.93g (0.2 mole) was added into a stirred 1 L jacketed three-necked round-bottom flask containing 468.3 g of a 41% solution of toluene in methylcyclohexane. The organic portion was washed with two 150 g portions 10% wt. NaOH, with phase separation at 67–69° C. Some delayed phasing out/precipitation was observed from the organic portion in this instance. The organic phase was washed with three 140 mL portions of water at 70° C., then separated from the aqueous layer. The recovery of organic phase was 582.4 g (94.9%) and the pH of the aqueous phase as measured was 7.

Part B: A portion of the same BPADP crude product 140.8 g (0.2 mole) was added into a stirred 1 L jacketed three-necked round-bottom flask containing a 500.8 g of a solution comprised of 58% toluene, and 42% methylcyclohexane. The organic portion was washed with two 150 g portions 10% NaOH, with a phase separation deemed acceptable for processing at 67–69° C. The organic was then washed with three 140 mL portions of water at 68° C., then separated from the aqueous layer. The recovery of organic phase was 622.5 g (97.02%), again with the aqueous phase pH measurement showing a value of 7. This organic phase was stripped of the MCH and analyzed by HPLC which showed only BPADP (51.8%), toluene (42.67%) oligomeric BPADP (n=2, 4.3%) and <0.01% isopropenylphenyl diphenylphosphate.

EXAMPLE X

In this Example, BPADP was purified and isolated using either solvent stripping or steam stripping. To a jacketed 12-L four-necked round-bottom flask with a bottom drain was added 3038 g of crude BPADP. To this mixture was added 5529 g of recycled MCH/toluene (50/50). The mixture was warmed to about 70° C. and washed with 700 g of 10 wt % aqueous caustic. The aqueous phase (902 g, pH=14) was separated and the organic phase was washed a second time with 700 g of 1 wt % aqueous caustic. The resultant aqueous phase (737 g, pH=14) was separated and the organic phase was again washed, this time with water (703 g). The aqueous phase (707 g, pH=9) was separated and the organic phase was again washed with water (700 g). The aqueous phase (699 g, pH=8) was removed and washed with water (700 g) for the third time. There was obtained 685 g of aqueous phase (pH=8) and 8172 g of clear colorless organic phase which turned cloudy on standing.

Solvent Strip

Part of the organic phase (4100 g) was removed, filtered (Whatman 2 paper) and stripped on a rotary evaporator at <90° C./2 torr. The last of the solvent was removed by holding the slightly cloudy colorless, viscous liquid for 7 hours at 160° C./2 torr in a vacuum oven. There was obtained 1378 g of BPADP. Analysis by HPLC showed 81.84% BPADP, 13.29% oligomer (n=2), 2.05% oligomer (n=3), 0.46% diphenylphosphate of BPA, <0.01% IPP, 1.9% TPP and an acidity measured by titration of <0.05% calculated as HCl.

Steam Strip

The remainder of the reaction mass was filtered. Part of the filtered reaction mass was added to a 3-L four-necked round-bottom flask. The reaction mixture was mechanically stirred and the solvent was removed at 200 torr. The solution of product to be stripped was added from an addition funnel on the 3-L flask as space permitted. When the pot temperature reached 105° C. at 200 torr, a sample of the reaction mixture was taken and found to contain 7.1 wt % toluene and 0.14 wt % MCH. To another addition funnel was added 127 g of water. The reaction mixture was held at about 100° C./200 torr and the water was added over a period of 1.0 hour. The water flashed over at about the same rate it was added. The reaction mixture was stirred for 3 hours while it was held at 120° C./100 torr. The stirred reaction mixture was then held at 150 to 160° C./100 torr for 3 hours. The product (1237 g) after in situ steam stripping was analyzed by HPLC which showed 81.51% BPADP; 13.54% of oligomer (n=2), oligomer (n=3), and diphenylphosphate of BPA; <0.01% IPP; 1.86% TPP; 0.17% DPP; 0.04% phenol; and an acidity measured by titration of <0.05% calculated as HCl.

EXAMPLE XI

This was another operation in which BPADP was purified and then isolated using solvent stripping or steam stripping. To a jacketed 12-L four-necked round-bottom flask with a bottom drain was added 3100 g of crude BPADP along with 1939 g of recycled MCH/Toluene (50/50) and 1415 g of both toluene and MCH. Analysis of the acidic crude BPADP showed 76.27% BPADP, 13.23% oligomer (n=2), 2.07% oligomer (n=3), 0.53% diphenylphosphate of BPA, <0.01% IPP, 1.98% TPP, 1.2% DPP, 3.98% phenol. The mixture was warmed to about 70° C. and washed using 704 g of 10 wt % aqueous caustic. The aqueous phase (810 g, pH=14) was separated and the resultant organic phase was washed with 702 g of 1 wt % aqueous caustic. This aqueous phase (715 g, pH=14) was separated and the organic phase was then washed with water (702 g). The aqueous phase (967 g, pH=9) was separated and the organic phase was washed a second time with water (718 g). This aqueous phase (710 g, pH=8) was removed and the organic phase was washed with water (712 g) for the third time. There was obtained 732 g of aqueous phase (pH=8) and 6459 g of clear colorless organic phase which turned cloudy on standing.

Solvent Strip

One half of the organic phase was removed, filtered (Whatman 2 paper) and stripped on a rotavap at<90° C./2 torr. The last of the solvent was removed by holding the slightly cloudy colorless, viscous liquid for 22 hours at 150° C./2 torr in a vacuum oven. There was obtained 1453 g BPADP. HPLC analyses showed 81.01% BPADP, 14.1% oligomer (n=2), 2.21% oligomeric (n=3), 0.32% diphenylphosphate of BPA, <0.01% IPP, 2.12% wt TPP, 0.14% DPP, 0.02% phenol. The acidity, determined by titration using 0. 1N NaOH, was <0.05% wt calculated as HCl.

Steam Strip

The remainder of the reaction mass was filtered. Part of the filtered reaction mass was added to a 3-L four-necked round-bottom flask. The reaction mixture was mechanically stirred and the solvent was removed at 200 torr. The solution of product to be stripped was added from an addition funnel on the 3-L flask as space permitted. To another addition funnel was added 127 g of water. The reaction mixture was held at about 100° C./200 torr and the water was added over a period of 29 minutes. The water flashed over at about the same rate it was added. The stirred reaction was then held at 150–160° C./100 torr for 3 hours, giving 1441 g BPADP as a slightly cloudy colorless liquid. HPLC data of the final steam stripped product showed 81.18% BPADP, 13.92% oligomer (n=2), 2.16% oligomer (n=3), 0.33% diphenylphosphate of BPA, <0.01% IPP, 2.13% TPP, 0.12% DPP, 0.06% phenol, and by titration, an acidity of <0.05% calculated as HCl.

HPLC Analysis Procedure

The HPLC method used to obtain the area % values reported herein uses UV detection at 254 nm with an acetonitrile/water gradient on a reverse phase C18 column. Area % values are calculated for all peaks in the chromatogram. External standard reference materials are available for the following impurities: DPP, Phenol, BPA, and TPP. Individual solutions of these reference materials, made up at concentrations of 100 ppm, are injected and analyzed. Response factors are calculated for each of these reference peaks to allow weight % values for these impurities to be calculated from the sample chromatograms. One impurity, IPP, has been determined to have a UV response significantly greater than the rest of the peaks in the chromatogram. This was determined using other analytical techniques. Since a reference standard is not available for this material, the area value of this peak may be divided by 8 and then area % values for the chromatogram are recalculated. In conducting these analyses, any suitable HPLC system equipped with a multisolvent delivery system capable of binary gradient elution, UV detection at 254 nm, automatic sample injector capable of 10 μL sample injection can be used. The HPLC instrument used to obtain the area % values reported herein was a Hewlett-Packard Model 1090.

Examples XII and XIII illustrate the use of an initial water wash or wash with an aqueous buffer solution before use of aqueous caustic washes. Example XIV illustrates the use of aqueous caustic washes under the same conditions but without use of such initial water or aqueous buffer wash.

EXAMPLE XII

Water Wash Prior to 10 wt % NaOH Wash

The reactor used was a 1000-mL jacketed round bottom flask with a bottom outlet. The flask was equipped with a mechanical agitator, a thermometer, and a condenser. Charged to the reactor were 387.36 grams of toluene/methylcyclohexane (MCH) mixture (50/50 wt/wt), 272.33 grams of crude bisphenol-A bis(diphenylphosphate) reaction mass, and 119.32 grams of water. After agitating for 30 minutes and settling for 30 minutes, the water which weighed 118.3 grams was separated easily from the organic solution. Phenolic impurities were removed from the product by washing with 119.60 grams of 10 wt % aqueous NaOH and then with 119.38 grams of 1 wt % aqueous NaOH. Both of these aqueous cuts were easy and clean, and weighed 129.81 and 118.65 grams, respectively. For purposes of analysis, each aqueous cut was acidified with 85% $H_3PO_4$ to pH of 1 and extracted twice with 100 grams of 50/50 (wt/wt) toluene/MCH used each time. HPLC analyses revealed losses of 0.04, 0.06, and 0.04 grams of bisphenol-A bis(diphenylphosphate) product, respectively, in the water, 10% NaOH, and 1% NaOH washes.

EXAMPLE XIII

Aqueous Buffer Wash Prior to NaOH Wash

The same reactor setup was used in this run as in Example XII. Charged to the reactor were 389.71 grams of toluene/MCH mixture, 275.56 grams of another portion of crude bisphenol-A bis(diphenylphosphate) reaction mass, and 101.26 grams of a buffer solution prepared from 215.95 grams of water, 2.10 grams of 85 wt % $H_3PO_4$, and 7.51 grams of 10 wt % aqueous NaOH. After agitating for 330 minutes, the pH of the aqueous layer was adjusted to a pH of 4.0 with 13.44 grams of 10% aqueous NaOH and 0.45 grams of 85% $H_3PO_4$. The weight of the aqueous layer from this buffer wash was 111.32 grams. The organic solution was then washed with 10% aqueous NaOH (122.84 grams) and then with 1% aqueous NaOH (120.28 grams). The 10% aqueous NaOH wash was clean and easy, with 132.85 grams of organic phase recovered. The 1% aqueous NaOH wash was also clean and easy, with 110.23 grams of the organic phase cut as a clear liquid and 14.31 grams of emulsion/rag. For purposes of analysis, the aqueous cuts were acidified with $H_3PO_4$ and extracted with toluene/MCH mixture. HPLC analyses revealed losses of 0.01, 0.10, and 1.47 grams of bisphenol-A bis(diphenylphosphate) product, respectively, in the buffer, 1 0% NaOH, and 1% NaOH washes.

EXAMPLE XIV

Using the same reactor setup as in Example XIII, the flask was charged with 384.87 grams of 50/50 (wt/wt) toluene/methylcyclohexane and 121.60 grams of 10 wt % NaOH. With the temperature of the mixture being maintained at 55° C. Crude bisphenol-A bis(diphenylphosphate) reaction mass (274.24 grams) at 70° C. was charged into the mixture. The contents were agitated at 55° C. for 30 minutes and then settled for 30 minutes. The bottom aqueous layer (138.92 grams) was separated from the organic layer through the bottom outlet. Another NaOH wash (1 wt % 119.80 grams) was done identically to the 10 wt % NaOH wash to remove the remaining phenol. The phase cut (146.15 grams) of this wash was not clean, with a lot of bubbles. For the purposes of analysis, each aqueous cut was acidified with 85% $H_3PO_4$ to pH of 1 and extracted twice with 100 grams of 50/50 (wt/wt) toluene/MCH used each time. The total amount of the extractant for the 10 wt % and 1 wt % NaOH washes were 226.43 and 228.90 grams, respectively. HPLC analyses of the extractants yielded losses of 4.66 and 9.36 grams of bisphenol-A bis(diphenylphosphate) product in the 10% and 1% NaOH washes, respectively.

In Example XV, which illustrates an overall process of this invention wherein an initial buffer wash is employed, all parts are by weight.

EXAMPLE XV

A washing vessel equipped with heating means and a drain valve and spout at the bottom is charged with 2023 parts of a methylcyclohexane/toluene mixture (50/50 wt/wt), 718 parts of water, and 7.2 parts of aqueous NaOH (25 wt %). The contents are mixed for 5 minutes at 45–55° C. A crude bisphenol-A bis(diphenylphosphate) reaction mass (~1360 parts) is then transferred into the vessel. After being at 50° C. for 5 minutes, the contents are allowed to settle for 5 minutes. The pH of the bottom aqueous phase is checked and adjusted to pH 5 with about 2.1 parts of phosphoric acid (85 wt %). After adjusting the pH, the agitator is restarted and allowed to run for 5 minutes. After allowing the vessel contents to settle, the bottom aqueous phase is drained off. To the remaining contents in the vessel (i. e., the organic phase), 357 parts of water and 239 parts of aqueous NaOH (25 wt %) are charged and the contents are mixed for 15 minutes with the temperature in the 50–60° C. range. The agitator is stopped, the contents are allowed to settle, and the bottom aqueous layer is drained off. The organic phase contents in the wash kettle are then washed in an identical fashion with 537 parts of water and 25 parts of aqueous NaOH. The neutralized organic product solution is then washed three times with 600–720 parts of water. To isolate the product, the organic phase contents in the vessel are heated to 100° C. under vacuum (50 mmHg absolute) to distill off the majority of the solvents (methylcyclohexane and toluene). To remove the remaining solvents, 57 parts of water are fed slowly into the vessel at a rate of about 2 parts per minute with the temperature and the pressure being maintained at 100° C. and 50 mmHg, respectively. The temperature is then increased to and maintained at 120° C. Solvent removal and drying of the product is completed when the liquid level in the distillate receiver is constant.

It is of interest to note that in a pair of operations under similar operating conditions in which in one case the initial aqueous buffer wash was employed whereas in other case it was not, the operation in which the buffer wash was used resulted in an 85% reduction in the amount of emulsion formation.

While this invention has been described in connection with the purification of impure or crude bisphenol-A bis (diphenylphosphate) of the formula given hereinabove, it is contemplated that the principles, operations, and advantages of this invention are applicable to other arylene bis (diarylphosphates) having similar impurities and solubilities, such as for example, bisphenol-A bis(diphenyl phosphates) in which the phenyl groups are, independently, (i) phenyl groups or (ii) alkylphenyl groups containing up to about 10 carbon atoms each, where at least one such group is an alkylphenyl group of (ii).

It will be seen from the foregoing description that a number of advantages and new features are provided by this invention. For example, the unique hydrocarbon solvent mixture used for preparing the initial solution of the impure or crude BPADP enables the dissolved crude product to be washed to remove impurities without high yield losses due to hydrolysis and subsequent emulsion formation. Indeed, the washing operation(s) in which the solution of the crude product in such solvent mixture using the alkaline aqueous wash solution makes possible optimal removal of acidity, color, phenolic impurities, DPP, residual catalyst (e.g., metals), and chlorides. In this connection, the importance of using the hydrocarbon solvent mixture as the medium for the washing of the crude product is made clear by the facts that:

1) attempts to wash the crude product without an organic solvent results in hydrolysis of the product during a NaOH wash which in turn causes significant emulsion formation;
2) use of a 100% aromatic hydrocarbon solvent such as toluene instead of the hydrocarbon solvent mixtures used pursuant to this invention forms a solution, but fails to provide enough density difference between the phases formed during the washing, and results in emulsion formation; and
3) use of a 100% cycloparaffinic solvent such as methylcyclohexane solvent instead of the hydrocarbon solvent mixtures used pursuant to this invention provides a suitable density difference, but fails to dissolve enough of the crude product, and results in hydrolysis and emulsion formation.

In short, the components of the hydrocarbon solvent mixtures used pursuant to this invention mutually cooperate with each other to provide a medium in which the specified alkaline washing(s) can be carried out without emulsion formation and with a resultant clean phase separation which greatly facilitates the phase separation(s).

To further reduce the risk of emulsion formation, the entire quantity of the crude product should be dissolved in the hydrocarbon solvent mixture. Solvent loading of about 25 to about 75 wt % of dissolved crude product results in homogeneous solutions of the crude product and thus contributes the prevention of emulsion formation at the wash operating temperatures in the range of about 25° C. to about 75° C. used pursuant to this invention. Failure to suitably coordinate solvent loading and wash operating temperature can result in problems. For example, the following benchmarks may be used in order to farther minimize the possibility of problems with solubility and emulsion formation:

1) when using a 42% crude loading in a mixed hydrocarbon solvent of this invention, the temperature should be kept above about 40° C.; and
2) higher solvent loadings enable operations at progressively lower wash operating temperatures.

Still other advantages and features of this invention relate to the use in preferred embodiments of in situ or live steam stripping for efficient removal of the hydrocarbon solvent mixtures used as the organic medium for the alkaline washes. The use or in situ generation of steam allows the solvent strip to be performed:

1) in less processing time—two hours versus 12 hours for standard flash at the same operating temperature; and
2) at lower temperatures and/or higher pressures—this either minimizes product degradation caused by higher temperatures or eliminates the need for more costly vacuum equipment (e.g., vacuum pumps and/or wiped film evaporators)

By conducting the process operations in an inert environment (such as a nitrogen blanket) pursuant to preferred embodiments of the invention haze formation or development of turbidity can be minimized.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. Although unlikely, the fact that a substance may lose its original identity through a chemical reaction, complex formation, solvation, or other transformation during the course of contacting, blending or mixing operations, if done in accordance with the disclosure hereof, is within the purview and scope of this invention.

Each and every patent or other publication referred to in any portion of this specification is incorporated into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of minimizing or preventing emulsion formation and suppressing hydrolytic product degradation during the purification of an impure bisphenol-A bis(diphenylphosphate) product mixture, which process comprises:
    a) mixing such impure product with a liquid hydrocarbon solvent comprising at least one aromatic hydrocarbon and at least one paraffinic hydrocarbon in proportions of such impure product to such liquid hydrocarbon solvent in the range of about 25:75 to about 75:25 to form a hydrocarbon solution;
    b) washing hydrocarbon solution from a) one or more times with an aqueous alkaline washing solution that has a specific gravity that differs from the specific gravity of the hydrocarbon solution by at least about 0.05 gram per cubic centimeter, after each such washing having the washed mixture settle into a purified organic phase and a separate aqueous phase, and separating these phases from each other, each such washing and separating being performed with the phases at a temperature in the range of about 25 to about 100° C.; and
    c) after completing the one or more washings and separations in b), washing the resultant purified organic phase one or more times with water to remove alkaline components from the hydrocarbon solution, after each such washing having the washed mixture settle into a less alkaline purified organic phase and a separate aqueous phase, and separating these phases from each other, each such washing and separating being performed with the phases at a temperature in the range of about 25 to about 100° C.

2. A process of claim 1 wherein the operations specified in b) are conducted at least twice, and the operations specified in c) are conducted at least two or three times.

3. A process of claim 1 further comprising removing hydrocarbon solvent from organic phase separated in c).

4. A process of claim 3 wherein removal of hydrocarbon solvent is carried out by flashing off hydrocarbon solvent from organic phase separated in c).

5. A process of claim 3 wherein removal of hydrocarbon solvent is carried out by steam distilling hydrocarbon solvent from organic phase separated in c).

6. A process of claim 3 wherein removal of hydrocarbon solvent is carried out by azeotropically distilling hydrocarbon solvent from organic phase separated in c).

7. A process of claim 1 further comprising removing residual amounts of water from organic phase separated in c).

8. A process of claim 1 wherein the hydrocarbon solvent used is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture.

9. A process of claim 1 wherein the hydrocarbon solvent used is a liquid mixture consisting essentially of (i) toluene and (ii) cyclohexane or methylcyclohexane, or both, in a weight ratio of (i):(ii) in the range of about 30:70 to about 70:30.

10. A process of claim 1 wherein the concentration of the hydrocarbon solution formed in a) is coordinated with the temperature used in the washing operation(s) in b), in accordance with the following benchmarks:
    1) when using a 42% crude loading in the mixed hydrocarbon solvent formed in a), the temperature in the washing operation(s) should be kept above about 40° C.; and
    2) higher solvent loadings enable operations at progressively lower wash operating temperatures.

11. A process of claim 1 wherein after settling in b), the washed purified organic phase is superposed on the separate aqueous phase.

12. A process of claim 1 wherein the hydrocarbon solvent used in a) is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture; wherein the operations specified in b) are conducted at least twice, and the operations specified in c) are conducted at least two or three times; and wherein removal of organic solvent is carried out by flashing off organic solvent from organic phase separated in c).

13. A process of claim 12 wherein removal of hydrocarbon solvent is carried out by steam distilling hydrocarbon solvent from an organic phase separated in c).

14. A process of claim 12 wherein removal of hydrocarbon solvent is carried out by azeotropically distilling hydrocarbon solvent from an organic phase separated in c).

15. A process of claim 12 wherein the hydrocarbon solvent used in a) is a liquid mixture consisting essentially of (i) toluene and (ii) cyclohexane or methylcyclohexane, or both, in a weight ratio of (i):(ii) in the range of about 30:70 to about 70:30.

16. A process of claim 12 wherein the concentration of the hydrocarbon solution formed in a) is coordinated with the temperature used in the washing operation(s) in b), in accordance with the following benchmarks:
    1) when using a 42% crude loading in the mixed hydrocarbon solvent formed in a), the temperature in the washing operation(s) should be kept above about 40° C.; and
    2) higher solvent loadings enable operations at progressively lower wash operating temperatures.

17. A process of claim 12 wherein the hydrocarbon solvent used in a) is a liquid mixture consisting essentially of (i) toluene and (ii) cyclohexane or methylcyclohexane, or both, in a weight ratio of (i):(ii) in the range of about 30:70 to about 70:30; wherein the concentration of the hydrocarbon solution formed in a) is coordinated with the temperature used in the washing operation(s) in b), in accordance with the following benchmarks:

1) when using a 42% crude loading in the mixed hydrocarbon solvent formed in a), the temperature in the washing operation(s) should be kept above about 40° C.; and 2) higher solvent loadings enable operations at progressively lower wash operating temperatures; and wherein removal of hydrocarbon solvent is carried out by steam distilling hydrocarbon solvent from an organic phase separated in c).

18. A process of minimizing or preventing emulsion formation and suppressing hydrolytic product degradation during the purification of an impure bisphenol-A bis(diphenylphosphate) product of the formula:

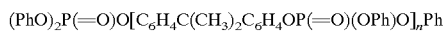

$(PhO)_2P(=O)O[C_6H_4C(CH_3)_2C_6H_4OP(=O)(OPh)O]_nPh$ where Ph is phenyl, $C_6H_4$ is a p-phenylene group, and n is a number in the range of 0 to about 5 with the provisos that (A) if the depicted phosphate is a single compound, then n is 1, 2, 3, 4, or 5, and (B) if the depicted phosphate is a mixture of such depicted phosphate esters in which the numerical values for n are not the same for each molecule of the mixture, then n can include, but need not include, zero, and is the average number for such mixture and is in the range of about 1 to below 5, which process comprises at least the following operations:

a) mixing such impure product with a liquid hydrocarbon solvent comprising at least one aromatic hydrocarbon and at least one paraffinic hydrocarbon in proportions of such impure product to such liquid hydrocarbon solvent in the range of about 25:75 to about 75:25 to form a hydrocarbon solution;

b) washing hydrocarbon solution from a) one or more times with an aqueous alkaline washing solution that has a specific gravity that differs from the specific gravity of the hydrocarbon solution by at least about 0.05 gram per cubic centimeter, after each such washing having the washed mixture settle into a purified organic phase and a separate aqueous phase, and separating these phases from each other, each such washing and separating being performed with the phases at a temperature in the range of about 25 to about 100° C.; and c) after completing the one or more washings and separations in b), washing the resultant purified organic phase one or more times with water to remove alkaline components from the hydrocarbon solution, after each such washing having the washed mixture settle into a less alkaline purified organic phase and a separate aqueous phase, and separating these phases from each other, each such washing and separating being performed with the phases at a temperature in the range of about 25 to about 100° C.

19. A process of claim 18 further comprising recovering purified bisphenol-A bis(diphenylphosphate) product from the final purified organic phase from the water washing in c).

20. A process of claim 18 wherein the liquid hydrocarbon solvent used is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture.

21. A process of claim 18 wherein the liquid hydrocarbon solvent used is a liquid mixture consisting essentially of (i) toluene and (ii) cyclohexane or methylcyclohexane, or both, in a weight ratio of (i):(ii) in the range of about 30:70 to about 70:30.

22. A process of claim 18 wherein the impure bisphenol-A bis(diphenylphosphate) product of said formula is a mixture of such depicted phosphate esters in which the numerical values for n are not the same for each molecule of the mixture, and wherein n is the average number for such mixture and is between 1 and about 2.

23. A process of minimizing or preventing emulsion formation and suppressing hydrolytic product degradation during the purification of an impure bisphenol-A bis (diphenylphosphate) product, which process comprises:

1) mixing (i) an aqueous buffer solution with a pH of less than about 5.5 or water, with (ii) the impure product in the presence of a liquid hydrocarbon solvent comprising at least one aromatic hydrocarbon and at least one paraffinic hydrocarbon in proportions of impure product to such liquid hydrocarbon solvent in the range of about 25:75 to about 75:25, and then having the mixture settle into an organic phase and a separate aqueous phase, and separating these phases from each other;

2) washing organic phase from 1) one or more times with an aqueous alkaline washing solution that has a specific gravity that differs from the specific gravity of the organic phase by at least about 0.05 gram per cubic centimeter, after each such washing having the washed mixture settle into a purified organic phase and a separate aqueous phase, and separating these phases from each other, each such washing and separating in 2) being performed with the phases at a temperature in the range of about 25 to about 100° C.; and 3) after completing the one or more washings and separations in 2), washing the resultant purified organic phase one or more times with water to remove alkaline components from the hydrocarbon solution, after each such washing having the washed mixture settle into a less alkaline purified organic phase and a separate aqueous phase, and separating these phases from each other, each such washing and separating in 3) being performed with the phases at a temperature in the range of about 25 to about 100° C.

24. A process of claim 23 wherein the operations specified in 2), are conducted at least twice, and the operations specified in 3) are conducted at least two or three times.

25. A process of claim 23 further comprising removing hydrocarbon solvent from organic phase separated in 3).

26. A process of claim 25 wherein removal of hydrocarbon solvent is carried out by flashing off hydrocarbon solvent from organic phase separated in 3).

27. A process of claim 25 wherein removal of hydrocarbon solvent is carried out by steam distilling hydrocarbon solvent from organic phase separated in 3).

28. A process of claim 25 wherein removal of hydrocarbon solvent is carried out by azeotropically distilling hydrocarbon solvent from organic phase separated in 3).

29. A process of claim 23 further comprising removing residual amounts of water from organic phase separated in 3).

30. A process of claim 23 wherein the hydrocarbon solvent used is a liquid hydrocarbon mixture comprising (i)

in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture.

31. A process of claim 23 wherein the hydrocarbon solvent used is a liquid mixture consisting essentially of (i) toluene and (ii) cyclohexane or methylcyclohexane, or both, in a weight ratio of (i):(ii) in the range of about 30:70 to about 70:30.

32. A process of claim 23 wherein the concentration of the hydrocarbon solution formed in 1) is coordinated with the temperature used in the washing operation(s) in 2), in accordance with the following benchmarks:
   1) when using a 42% crude loading in the mixed hydrocarbon solvent formed in 1), the temperature in the washing operation(s) should be kept above about 40° C.; and
   2) higher solvent loadings enable operations at progressively lower wash operating temperatures.

33. A process of claim 23 wherein after settling in 2), the washed purified organic phase is superposed on the separate aqueous phase.

34. A process of claim 23 wherein the hydrocarbon solvent used in 1) is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture; wherein the operations specified in 2) are conducted at least twice, and the operations specified in 3) are conducted at least two or three times; and wherein removal of organic solvent is carried out by flashing off organic solvent from organic phase separated in 3).

35. A process of claim 34 wherein removal of hydrocarbon solvent is carried out by steam distilling hydrocarbon solvent from an organic phase separated in 3).

36. A process of claim 34 wherein removal of hydrocarbon solvent is carried out by azeotropically distilling hydrocarbon solvent from an organic phase separated in 3).

37. A process of claim 34 wherein the hydrocarbon solvent used in 1) is a liquid mixture consisting essentially of (i) toluene and (ii) cyclohexane or methylcyclohexane, or both, in a weight ratio of (i):(ii) in the range of about 30:70 to about 70:30.

38. A process of claim 34 wherein the concentration of the hydrocarbon solution formed in 1) is coordinated with the temperature used in the washing operation(s) in 2), in accordance with the following benchmarks:
   1) when using a 42% crude loading in the mixed hydrocarbon solvent formed in 1), the temperature in the washing operation(s) should be kept above about 40° C.; and
   2) higher solvent loadings enable operations at progressively lower wash operating temperatures.

39. A process of claim 34 wherein the hydrocarbon solvent used in 1) is a liquid mixture consisting essentially of (i) toluene and (ii) cyclohexane or methylcyclohexane, or both, in a weight ratio of (i):(ii) in the range of about 30:70 to about 70:30; wherein the concentration of the hydrocarbon solution formed in 1) is coordinated with the temperature used in the washing operation(s) in 2), in accordance with the following benchmarks:
   1) when using a 42% crude loading in the mixed hydrocarbon solvent formed in 1), the temperature in the washing operation(s) should be kept above about 40° C.; and
   2) higher solvent loadings enable operations at progressively lower wash operating temperatures; and
wherein removal of hydrocarbon solvent is carried out by steam distilling hydrocarbon solvent from an organic phase separated in 3).

40. A process of claim 23 wherein the operations specified in 2) are conducted at least twice, and the operations specified in 3) are conducted at least two or three times, and wherein the concentration of the base in the first aqueous alkaline washing solution is higher than the concentration(s) of the base in the ensuing aqueous alkaline washing solution(s).

41. A process of claim 40 wherein the hydrocarbon solvent used is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture.

42. A process of claim 40 wherein the hydrocarbon solvent used is a liquid mixture consisting essentially of (i) toluene and (ii) cyclohexane or methylcyclohexane, or both, in a weight ratio of (i):(ii) in the range of about 30:70 to about 70:30.

43. A process of claim 23 wherein the operations specified in 2) are conducted at least twice, and the operations specified in 3) are conducted at least two or three times, and wherein the aqueous alkaline washing solutions are aqueous sodium hydroxide solutions.

44. A process of claim 43 wherein the hydrocarbon solvent used is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture.

45. A process of claim 43 wherein the hydrocarbon solvent used is a liquid mixture consisting essentially of (i) toluene and (ii) cyclohexane or methylcyclohexane, or both, in a weight ratio of (i):(ii) in the range of about 30:70 to about 70:30.

46. A process of claim 43 wherein the concentration of the base in the first aqueous sodium hydroxide washing solution is higher than the concentration(s) of the sodium hydroxide in the ensuing aqueous alkaline washing solution(s).

47. A process of claim 46 wherein the hydrocarbon solvent used is a liquid hydrocarbon mixture comprising (i) in the range of about 10 to about 70 wt % percent of at least one aromatic hydrocarbon, and (ii) in the range of about 10 to about 70 wt % percent of at least one cycloparaffinic hydrocarbon, with the total of (i) and (ii) being at least 90 wt % of the liquid hydrocarbon mixture.

48. A process of claim 46 wherein the hydrocarbon solvent used is a liquid mixture consisting essentially of (i) toluene and (ii) cyclohexane or methylcyclohexane, or both, in a weight ratio of (i):(ii) in the range of about 30:70 to about 70:30.

49. A process of claim 1 wherein said at least one paraffinic hydrocarbon consists essentially of one or more cycloparaffinic hydrocarbons.

50. A process of claim 18 wherein said at least one paraffinic hydrocarbon consists essentially of one or more cycloparaffinic hydrocarbons.

51. A process of claim 23 wherein said at least one paraffinic hydrocarbon consists essentially of one or more cycloparaffinic hydrocarbons.

* * * * *